United States Patent [19]

Small et al.

[11] Patent Number: 4,673,525
[45] Date of Patent: Jun. 16, 1987

[54] ULTRA MILD SKIN CLEANSING COMPOSITION

[75] Inventors: Leonard E. Small; Paul H. Garrison, Jr.; William M. Winkler, all of Cincinnati; Sharon A. Seaman, Milford; Alyce J. Papa, Wyoming, all of Ohio

[73] Assignee: The Procter & Gamble Company, Cincinnati, Ohio

[21] Appl. No.: 733,670

[22] Filed: May 13, 1985

[51] Int. Cl.⁴ .......................... C11D 9/02; C11D 9/60
[52] U.S. Cl. ..................................... 252/132; 252/108; 252/117; 252/121; 252/122; 252/174.17; 252/DIG. 2; 252/DIG. 5; 252/DIG. 7; 252/DIG. 16
[58] Field of Search ............... 252/108, 117, 121, 122, 252/132, 174.17, DIG. 2, DIG. 5, DIG. 7, DIG. 16

[56] References Cited

U.S. PATENT DOCUMENTS

| 2,894,912 | 7/1959 | Geitz | 252/121 |
|---|---|---|---|
| 2,979,465 | 4/1961 | Parran et al. | 252/546 |
| 3,043,778 | 7/1962 | Kelly | 252/121 |
| 3,598,746 | 8/1971 | Kaniecki et al. | 252/118 |
| 3,703,481 | 11/1972 | Barker et al. | 252/90 |
| 3,761,418 | 9/1973 | Parran, Jr. | 252/106 |
| 4,012,341 | 3/1977 | Orshitzer et al. | 252/90 |
| 4,180,470 | 12/1979 | Tokosh et al. | 252/121 |
| 4,234,464 | 11/1980 | Morshauser | 252/117 |
| 4,292,212 | 9/1981 | Melby | 252/547 |
| 4,338,211 | 7/1982 | Stiros | 252/541 |
| 4,477,375 | 10/1984 | Grollier | 252/542 |
| 4,491,539 | 1/1985 | Hoskins et al. | 252/541 |
| 4,574,053 | 3/1986 | Kinsman et al. | 252/134 |

FOREIGN PATENT DOCUMENTS 1065460  4/1967  United Kingdom ......... 252/DIG. 5

OTHER PUBLICATIONS

"The Soap Chamber Test: A New Method for Assessing the Irritancy of Soaps," Frosch & Kligman, Journal of the American Academy of Dermatology, 1979, pp. 35-41.

Primary Examiner—Robert A. Wax
Attorney, Agent, or Firm—Leonard Williamson; Ronald L. Hemingway; Richard C. Witte

[57] ABSTRACT

Disclosed is an ultra mild skin cleansing composition comprising: mild synthetic surfactants, moisturizers, polymeric skin feel and mildness aids and selected levels of soap. An ultra mild skin cleansing bar is provided which is clinically milder on the skin than water.

27 Claims, 6 Drawing Figures

ULTRA MILD SKIN CLEANSING COMPOSITION

TECHNICAL FIELD

This invention relates to mild skin cleansing compositions.

BACKGROUND OF THE INVENTION

This invention relates to mild skin cleansers. More particularly, this invention relates to skin cleansers comprising synthetic surfactants, moisturizers, polymeric skin feel and mildness aids and soap.

The cleansing of skin with surface-active cleansing preparations has become a focus of great interest. Many people wash and scrub their skin with various surface-active preparations several times a day. Ideal skin cleansers should cleanse the skin gently, causing little or no irritation, without defatting the overdrying the skin or leaving it taut after frequent routine use. Most lathering soaps, liquids and bars included, fail in this respect.

Synthetic detergent bars, frequently referred to as "syndet bars," are well known and are becoming increasingly popular. However, widespread replacement of soap bars by syndet bars has not so far been possible for a variety of reasons, primarily the poor physical characteristics of syndet bars as compared to soap bars, e.g., smear or bar messiness and lather quality.

Certain synthetic surfactants are particularly mild. However, a major drawback of most mild synthetic surfactant systems when formulated for skin cleansing is poor lather performance, when compared to the highest bar soap standards (bars which are rich in coconut soap and superfatted). On the other side, the use of known high sudsing anionic surfactants with lather boosters can yield acceptable lather volume. Unfortunately, however, the highest sudsing anionic surfactants are, in fact, poor in clinical skin mildness. Surfactants that are among the mildest, such as sodium lauryl glyceryl ether sulfonate, (AGS), are marginal in lather. It will be appreciated that these two factors make the surfactant selection, the lather and the skin feel benefit formulation process, a delicate balancing act.

Similarly, optimization of bar firmness also requires a delicate balancing act with respect to maintaining acceptable lather and mildness, although as a single variable, bar firmness is accomplished through a fairly straightforward process with adjustments to levels of fillers, binders, etc., such as free fatty acids.

It is known that moisturizers provide skin conditioning benefits. For example, it is known that glycerin and/or free fatty acids are added to bars or liquid cleansing products for skin benefits.

Likewise, polymeric skin feel aids are known to those knowledgeable in the art for providing unique tactile characteristics to both the lather and the skin during rinsing.

For background, examples of liquid cleansing compositions are disclosed in the following references. U.S. Pat. No. 4,338,211, Stiros, issued July 6, 1982, discloses liquid skin cleanser with 2.3% to 3% AGS, the polymer JR-400 and small amounts of free fatty acid plus a fatty acid alkylolamide as lather boosting agents. Compositions containing the surfactants AGS and sarcosinate are not disclosed. Also, U.S. Pat. No. 4,491,539, James J. Hoskins and Adriaan Kessler, issued Jan. 1, 1985, discloses liquid cleansing products comprising about 5% to 30% of surfactant, about 0.1% to about 1.0% of guar material, about 0.15% to about 1.0% of nonionic carboxyvinyl polymer, and water. Exemplary compositions containing mild surfactants in general and, specifically, the surfactants AGS and sarcosinate are not disclosed. Another background reference is British Pat. No. 2,103,236A, Colgate, Feb. 16, 1984, which discloses a liquid detergent containing guar gum, a ternary surfactant mixture including betaine. AGS is not used.

U.S. Pat. No. 2,894,912, Geitz, issued July 14, 1959, for "Isethionate Detergent Bar," discloses a detergent bar consisting essentially of from 30–70% of water-soluble alkali metal detergent salts of esters of isethionic acid with mixed aliphatic fatty acids having from 6 to 18 carbon atoms and an iodine value of less than 20, of which mixed acids at least 75% have from 12 to 18 carbon atoms and up to 25% have from 6 to 10 carbon atoms, from 2–10% of at least one water-soluble suds-boosting detergent salt selected from the group consisting of alkali metal and organic amine higher aliphatic fatty alcohol sulfates, alkyl aryl sulfonates, and higher aliphatic fatty acid taurides, from about 1% to about 9% water, from about 2.5% to about 25% of water-soluble higher fatty acid soap, and from 10–40% of at least one higher fatty acid having from about 12 to about 25 carbon atoms as a binder and plasticizer, said bar having a pH within the range from 6 to 8, measured as a 10% aqueous solution of the bar composition at 35° C. This patent does not teach the use of polymeric skin feel aids nor the use of other mild synthetics.

U.S. Pat. No. 4,234,464, Morshauser, issued Nov. 18, 1980, for "Detergent Bar Composition and Binder Therefor," discloses a detergent bar in Example 6 which comprises: 45% sodium cocoyl isethionate, 5% alkyl amide, 37.5% stearic acid, 5.0% hydrogenated tallow glycerides, and 1% Polymer JR. Morshauser teaches that his detergent bars can contain up to 5% soap "without substantial detriment." This patent also teaches the use of up to 1.5% cationic polymer.

U.S. Pat. No. 4,012,341, Orshitzer et al., issued Mar. 15, 1977, for a "Unique All Synthetic Detergent Shampoo Bar," discloses a bar comprising a mixture of anionic and nonionic detergents. Examples 2 and 4 use 1% JR-400 in bars primarily based on sodium lauryl sulfate, which is an unacceptable surfactant for the present invention.

U.S. Pat. No. 3,761,418, Parran, Jr., issued Sept. 25, 1973, for "Detergent Compositions Containing Particle Deposition Enhancing Agents," discloses detergent compositions including a bar which contains 1% JR-400. However, the main surfactant is alkyl sulfate, which is unacceptable for the mild skin cleanser of the present invention.

Thus, in view of the above, it will be appreciated that rather stringent requirements for skin cleansers limit the choice of surface-active agents and final formulations represent some degree of compromise. Mildness is often obtained at the expense of effective cleansing and lathering. Conversely, mildness may be sacrificed for either preferred lathering characteristics, bar firmness, product stability, or all of these.

OBJECTS OF THE INVENTION

This invention represents a skin cleansing composition which provides ultra skin mildness, excellent lather and bar firmness. Therefore, one object of this invention is the development of skin cleansing compositions which exhibit superior skin mildness and moisturization while maintaining acceptable lather and bar properties.

Another object of the present invention is the development of skin cleansers having skin feel and mildness benefits.

Other objects will become apparent from the detailed description below.

SUMMARY OF THE INVENTION

This invention is an ultra mild skin cleansing composition comprising: mild synthetic surfactants, moisturizers, polymeric skin feel and skin mildness aids and soap. An ultra mild skin cleansing bar is provided which is clinically milder on the skin than water. Thus, the present invention offers a remarkable combination of desirable properties to skin cleansing formulations. The invention provides a mild, effective skin cleansing composition having superior moisturization and skin mildness and skin feel benefits. The composition leaves the skin feeling moist, soft and smooth after washing. A preferred cleansing product is a toilet bar having 20–70% mild surfactant, 10–40% moisturizer, 0.1–5% polymeric skin feel and mildness aid and 5.5–25% soap.

DETAILED DESCRIPTION OF THE INVENTION

The invention relates to an ultra mild skin cleansing composition with superior moisturization, excellent skin feel benefits and lather performance. This mild cleansing composition is believed to provide superior moisturization, less skin irritation and facial tautness than commercially available toilet soap bars, synthetic toilet bars or other known surfactant based specialty skin cleansing products such as liquids and creams. Ultra mild liquids and creams can be made by diluting the mild cleansing compositions disclosed herein with 20–70% water. The composition of this invention leaves the skin feeling soft and smooth after washing and is also clinically milder than washing with water alone. The percentages herein are on a total composition weight basis unless otherwise specified.

A preferred composition contains: 10–40% moisturizer, e.g., free fatty acids; 40–70% of mild surfactants, e.g., alkyl glyceryl ether sulfonate (AGS) plus a co-surfactant selected from anionic alkyoyl(acyl)sarcosinates; 0.1–4% polymeric skin feel and skin mildness aids selected from cationic polymers including guar gums, cellulosic resins; homopolymers and copolymers of dimethyldiallylammonium chloride and nonionic guar gums, and soap at a level of 5.5–20%.

The Surfactant

A mild surfactant as defined herein includes those which have a Relative Skin Barrier Penetration Value as defined hereinbelow of as close to zero as possible up to about 75. The mild synthetic surfactant is present in the composition at a level of 20–70%, preferably 40–70% and more preferably 50–65%. Also the synthetic surfactant and soap have ratios of 2:1 to 12:1, preferably 4:1 to 10:1 and more preferably 6:1 to 9:1.

Preferred mild anionic and amphoteric surfactants used in this invention include suitable alkyl glyceryl ether sulfonate (AGS), anionic acyl sarcosinates, methyl acyl taurates, N-acyl glutamates, acyl isethionates, alkyl sulfosuccinate, alkyl phosphate esters, ethoxylated alkyl phosphate esters, trideceth sulfates, protein condensates, mixtures of ethoxylated alkyl sulfates and alkyl amine oxides, betaines, sultaines, and mixtures thereof. Included in the surfactants are the alkyl ether sulfates with 1 to 12 ethoxy groups, especially ammonium and sodium lauryl ether sulfates. Alkyl chains for these surfactants are $C_8$–$C_{22}$, preferably $C_{10}$–$C_{18}$. Alkyl glucosides and methyl glucose esters are preferred mild nonionics which may be mixed with at least one of said mild anionic or amphoteric surfactants in the compositions of this invention.

A preferred primary mild surfactant is sodium coco glyceryl ether sulfonate which is mild and relatively nonirritating to the skin. This has been demonstrated in in vitro nonclinical mildness testing. While desirable to incorporate into a skin cleanser for its mildness properties, this coco AGS alone does not provide optimum lather creaminess. A sodium 90/10 coconut/tallow alkyl AGS distribution is preferred for creaminess. Salts other than the sodium salt such as TEA-, ammonium- and K-AGS and chain length distributions other than 90/10 coconut/tallow are usable at moderate levels. Also, some soap is added to improve lather volume and speed of lathering. Certain secondary co-surfactants used in combination with AGS can also provide a creamier and more stable lather. These secondary surfactants must also be intrinsically mild. One secondary surfactant that has been found to be especially desirable is sodium lauroyl sarcosinate (trade name Hamposyl L, made by Hampshire Chemical).

The amphoteric betaines and sultaines can be used as the sole surfactant, but are more preferred as a co-surfactant. Nonionics cannot be used as the sole surfactant in this product because of their low foaming ability; however, they can be incorporated as a co-surfactant.

In Vitro Skin Barrier Penetration Test

Introduction

The skin barrier penetration test (see test apparatus in FIG. 1) is used to screen mild surfactants from nonmild surfactants. In this test the milder the surfactant, the lesser the skin barrier 4 is destroyed. Skin barrier destruction is measured by the relative amount of radio-labeled water ($^3$H-$H_2$O) which passes from the test solution 3 through the skin epidermis 5 into the distilled water contained in the diffusate chamber 6. (This test is also described by T. J. Franz in the J. Invest. Derm., 64, pp. 190–195, 1975.)

Test Apparatus

Figure 1:
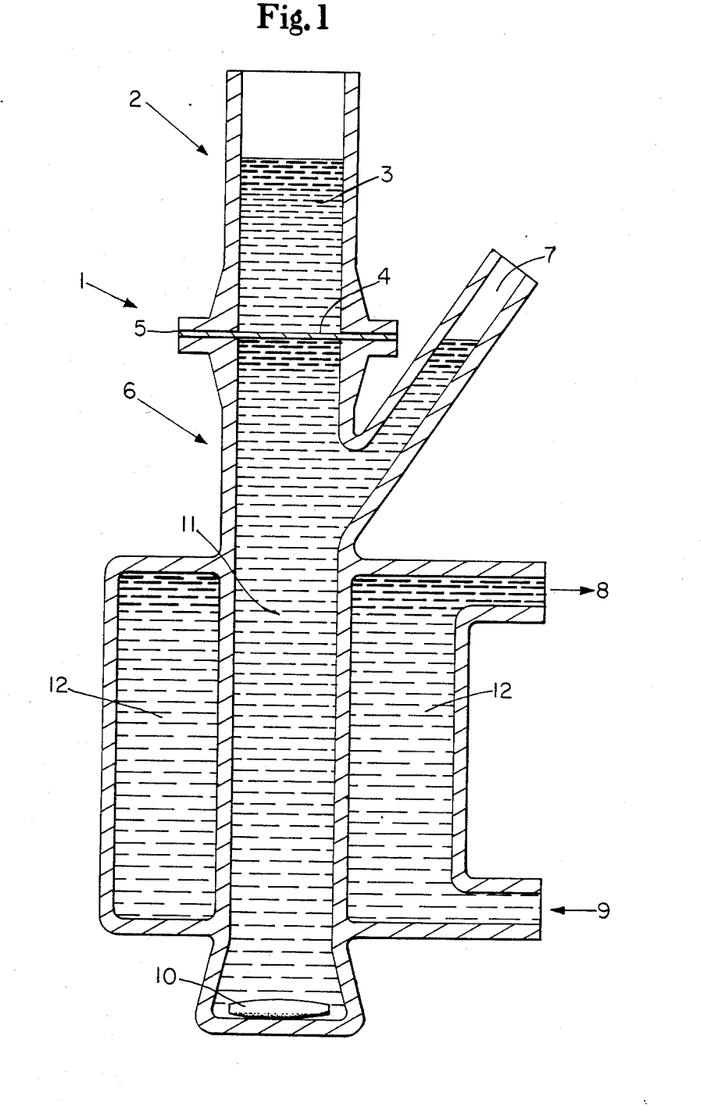
FIG. 1 shows a static diffusion cell diagram.

The skin barrier penetration test utilizes a static diffusion cell 1 diagrammed in FIG. 1. When studying surfactants which are not soluble at room temperature, water-jacketed cell tops (not shown) are used to hold the test solution 3 reservoir 2 at a different temperature than the diffusate chamber 6.

Human skin epidermis 5 is placed on the flat area of the diffusate chamber 6 and the diffusate chamber 6 is filled with distilled water 11 for collection of the transported radio-labeled water. The diffusate chamber 6 is surrounded by a water jacket 12. Temperature control is provided by circulating water bath (outflow 8 and inflow 9) pumped from a water bath at a predetermined temperature. When applicable, a jacketed top is connected to a second circulator/temperature bath. The diffusate chamber 6 is typically maintained at 25° C. An O-ring joint clamp secures the test solution reservoir 2, sandwiching the skin epidermis 5 in between it and the diffusate chamber 6.

This test uses cells which have a diffusion area of 0.20 cm$^2$. The diffusate chamber 6 holds approximately 5 ml. The bottom of the chamber 6 is flattened to allow spinning of a small magnetic stirring bar 10. The bars 10 are spun by a series of permanent magnets attached to individual electric motors. The motors turn at 300 rpm.

The test solution reservoir 2 holds approximately 1 ml of test solution 3. During testing the tops of reservoir 2 are sealed with Parafilm to inhibit evaporation and prevent spillage.

Skin Epidermis Preparation

Prior to testing, the skin epidermis is separated from the whole skin. The whole skin is thawed to room temperature and adipose tissue (cellular fat) is removed by surgical scalpel to the adipose-dermal junction. This "defatted" skin is immersed in 60° C. water for 80 seconds. This heat treatment makes possible the separation of the epidermis from the dermis at their junction. The epidermis is placed on a sheet of aluminum foil and rinsed with hexane for 5 seconds to remove excess fat globules still clinging to the surface. It is then sprayed with distilled water for 5 seconds to wash away the hexane. The epidermis sample is wrapped in Saran Wrap ®, placed in an aluminum pouch, and frozen in a standard freezer until needed.

Test Procedure

The following discussion describes a typical skin barrier penetration test. There are 30 cells per test, 5 replicates per treatment. This permits testing of 5 surfactant solutions plus a water control. Due to large variability in percutaneous transport (site to site and individual to individual), the water control is a mandatory reference point for each experiment.

Dose test solutions are prepared on a weight/weight basis on an analytical (±0.0001 g) balance. Since each static diffusion cell 1 is dosed with 500 μl, a minimum of 3 ml of each test solution 3 should be prepared (5 doses +standard). Each solution is spiked with $^3$H-H$_2$O to an approximate activity of 1.8 μCi/ml dosing solution. This insures a sufficient level of $^3$H transport for the sampling interval (2 hours).

During sample collection, the entire volume of the diffusate chamber 6 is emptied through the sampling port 7, rinsed, and refilled with fresh distilled water 11. Samples are collected at 2, 4, 6, 8 and 24 hours after initial dosing. The sample plus rinse is emptied into a scintillation vial, brought to 7 ml total volume and analyzed by liquid scintillation counting.

Standards are included in each sample. One hundred microliters (in duplicate) are placed in a scintillation vial and brought to 7 ml total volume with distilled water. The counts per minute (cpm) for diffusate samples are converted to equivalent mg water using the relation $$\frac{\text{mg water}}{\text{vial}} = \text{cpm sample} \times \frac{\text{mg water standard}}{\text{cpm standard}}$$

The "water flux" is computed as a total sum penetrant using standard programs on a Tektronix 4052A computer. It is important to realize that this "water flux" is a mg water equivalent of the $^3$H flux. It does not represent a net water flux, since water is diffusing in both directions in this experiment. The relative flux (vs. water control) is an indication of barrier integrity.

Skin Barrier Penetration Test Values for AGS and cocoyl isethionate are given in Table 1. Water and sodium dodecylsulfate ("SDS") are the mild and harsh controls, respectively. The test results are expressed in terms of the total amount of water penetrating through the skin in 24 hours. These amounts have also been converted to a relative scale (see Table 1) with water set to zero, SDS to 100, and AGS and isethionate interpolated in between.

TABLE 1

| | Skin Barrier Penetration | |
|---|---|---|
| Treatment | Total mg Water Penetrating the Skin in 24 Hours | Relative Skin Barrier Penetration Value |
| Water Control | 12.0 ± 3.6 | 0 |
| 1% AGS[a] | 22.8 ± 7.9 | 9 |
| 1% Cocoyl Isethionate | 60.3 ± 17.7 | 40 |
| 1% SDS[b] - Reference | 131.7 ± 68.0 | 100 |

[a]AGS is sodium coco AGS
[b]SDS is sodium dodecylsulfate

A mild surfactant as defined herein includes those which have a Relative Skin Barrier Penetration Value of as close to zero as possible. Most mild surfactants have Values of from about 7 to about 75, preferably 50 or less, and more preferably 40 or less. Surfactants which have Relative Skin Barrier Penetration Values of greater than 75 can be used along with the mild surfactant at low levels in the compositions of this invention, so long as their use does not significantly change the clinical skin mildness of the total skin cleansing composition.

Moisturizers/Emollients

Moisturizers are included to provide the skin conditioning benefits and to improve the mildness of the product. The selection of the levels and types of moisturizers to be incorporated into the product is made without adversely affecting the stability of the product or its in-use characteristics, thereby delivering good moisturization and lather.

The term "moisturizer" is often used within the cosmetic industry without very exact definition. The term is sometimes used as synonymous with emollient, and is then meant to describe a material which imparts a smooth and soft feeling to the skin surface.

There are two ways of reducing water loss from the stratum corneum. One is to deposit on the surface of the skin an occlusive layer which reduces the rate of evaporation. The second method is to add nonocclusive hygroscopic substances to the stratum corneum which will retain water, and make this water available to the stratum corneum to alter its physical properties and produce a cosmetically desirable effect. Nonocclusive moisturizers also function by improving the lubricity of the skin.

Both occlusive and nonocclusive moisturizers can work in the present invention. Some examples of moisturizers are long chain fatty acids, liquid water-soluble polyols, glycerin, propylene glycol, sorbitol, polyethylene glycol, ethoxylated/propoxylated ethers of methyl glucose (e.g., methyl gluceth-20) and ethoxylated/propoxylated ethers of lanolin alcohol (e.g., Solulan-75).

The moisturizers useful in the present invention are used at a level of 10% to 40% by weight of the composition. The preferred and more preferred levels of moisturizers are, respectively, 10% to 30% and 12% to 25%. The preferred moisturizers are the coco and tallow fatty acids. Some other preferred moisturizers are the nonocclusive liquid water-soluble polyols and the essential amino acid compounds found naturally in the skin. The most preferred moisturizer is a mixture of stearic and lauric acids having a ratio of from 2:1 to 1:1. These moisturizers also aid in solid bar integrity at said levels. The moisturizer, at these levels, provides superior moisturization. In the composition of this invention the high level of moisturizer with soap can also provide an enhanced lather and mildness.

The moisturizer to soap ratios are preferably 1:1 to 7:1 and, more preferably, 1:1 to 4:1.

Other preferred nonocclusive moisturizers are compounds found to be naturally occurring in the stratum corneum of the skin, such as sodium pyrrolidone carboxylic acid, lactic acid, urea, L-proline, guanidine and pyrrolidone. Examples of other nonocclusive moisturizers include hexadecyl, myristyl, isodecyl or isopropyl esters of adipic, lactic, oleic, stearic, isostearic, myristic or linoleic acids, as well as many of their corresponding alcohol esters (sodium isostearoyl-2-lactylate, sodium capryl lactylate), hydrolyzed protein and other collagen-derived proteins, aloe vera gel and acetamide MEA.

Some occlusive moisturizers include petrolatum, mineral oil, beeswax, silicones, lanolin and oil-soluble lanolin derivatives, saturated and unsaturated fatty alcohols such as behenyl alcohol, squalene and squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Other examples of both types of moisturizers are disclosed in "Emollients—A critical Evaluation," by J. Mausner, Cosmetics & Toiletries, May 1981, incorporated herein by reference.

The Polymeric Skin Feel and Skin Mildness Aids

The polymeric skin feel and mildness aids useful in the present invention are the cationic, anionic, amphoteric, and the nonionic polymers used in the cosmetic field. Reduced skin irritation benefits as measured by patch testing of cationic and nonionic types of polymers are set out in "Polymer JR for Skin Care" Bulletin, by Union Carbide, 1977. The cationics are preferred over the others because they provide better skin feel benefits. Examples of the cationic polymers and the nonionic polymers useful in the present invention are set out below.

The amount of polymeric skin feel and mildness aids found useful in the composition of the present invention is from about 0.01% to about 5%, preferably from about 0.3% to about 4%. In bar compositions with less than 5.5% soap, the polymer is used at a level of 2% to 5%, preferably 3% or more. The soap to polymer presence in the composition of this invention preferably has a stoichiometric ratios of about 1:1 to 14:1, preferably 4:1 to 10:1 on a charge basis.

In order to achieve superior skin mildness and moisturization for this composition, it was discovered that a combination of moisturizer (10-40% in the composition) and a selected polymeric ingredient, e.g., Polymer JR-400, made by Union Carbide Corporation, is required.

Other types of high molecular weight polymeric skin feel and skin mildness aids, such as nonionic guar gums, Merquats 100 and 550, made by Merck & Co., Inc; JAGUAR C-14-S made by Stein Hall; Mirapol A15 made by Miranol Chemical Company, Inc.; and Galactasol 811, made by Henkel, Inc.; plus others, are usable. The polymer also provides enhanced creamy lather benefits.

The nonionic polymers found to be useful include the nonionic polysaccharides, e.g., nonionic hydroxypropyl guar gums, offered by Celanese Water Soluble Polymers, a Division of Celanese Corp. A preferred nonionic hydroxypropyl guar gum material is JAGUAR ® HP-60 having molar substitution of about 0.6. Another class of useful nonionics is the cellulosic nonionic polymers, e.g., HEC and CMC.

The cationic polymers employed in this invention also provide a desirable silky, soft, smooth in-use feeling. The preferred level for this invention is 0.1-5% of the composition. While not being bound to any theory, it is believed that cationic polymers chemically interact with the anionic surfactants (e.g., AGS and sarcosinates) to form complexes which may enhance the mildness to skin characteristics of the already mild surfactants. Also, there is reason to believe that the positively charged cationic polymers can bind with negatively charged sites on the skin to provide a soft skin feel after use. Not to be bound by any theory, it is believed that the greater the charge density of the cationic polymer, the more effective it is for skin feel benefits.

Other suitable cationic polymers are copolymers of dimethylaminoethylmethacrylate and acrylamide and copolymers of dimethyldiallylammonium chloride and acrylamide in which the ratio of the cationic to neutral monomer units has been selected to give a copolymer having a cationic charge. Yet other suitable types of cationic polymers are the cationic starches, e.g., Sta-Lok ® 300 and 400 made by Staley, Inc.

A more complete list of cationic polymers useful in the present invention is described in U.S. Pat. No. 4,438,095, to Grollier/Allec, issued Mar. 20, 1984, incorporated herein by reference. Some of the more preferred cationics are listed in Col. 3, section 2; Col. 5, section 8; Col. 8, section 10; and Col. 9, lines 10–15 of the Grollier/Allec patent, incorporated herein by reference.

Soaps

Soaps are included in the compositions of this invention for improved lather, particularly under heavy soil loads. It is also surprising that the soap as used in the compositions of this invention provide clinical benefits for less skin dryness at levels up to 25% and less skin irritation (erythema) at levels up to 15%.

Soaps can be used at levels of 5.5-25%, preferably 6-15%, and most preferably at a level of 6-8%. The soaps are preferably made in situ via adding a base, e.g., NaOH, to convert free fatty acids in the composition mix. A minor amount of soap, about 0.1-0.5% as shown in Tables 2, 3 and 5, is present as a by-product of the synthetic surfactant. See the process for making an ultra mild bar set out below.

The preferred ultra mild skin cleansing composition is a bar comprising: 20-50% mild synthetic surfactant; 10-40% moisturizer; 0.1-5% polymeric skin feel aid, and 5.5-25% soap; wherein the synthetic surfactant and soap has a ratio of from 2:1 to 12:1; the moisturizer to soap has a ratio of from 1:1 to 7:1; and the soap to polymer has a stoichiometric ratio of from about 1:1 to about 14:1 on a charge basis. Preferably the synthetic to soap ratio is 4:1 to 10:1, and more preferably 6:1 to 9:1. The preferred moisturizer to soap ratio is from 2:1 to 4:1. The preferred soap to polymer stoichiometric ratio is from 4:1 to 10:1.

The soap is preferably made in situ from free fatty acids and a base selected from magnesium hydroxide and potassium hydroxide, preferably sodium hydroxide and triethanolamine. The preferred soap level is 6–15% of the composition, particularly in ultra mild skin cleansing compositions which contain from 10–30% fatty acids. Particularly preferred fatty acids are mixtures of stearic and lauric acids having a ratio of from 2:1 to 1:1.

Optionals

The usual optionals can be used in the composition of the present invention.

Perfumes may be used in formulating the skin cleansing products, generally at a level of about 0.1% to about 1.5% of the composition. Colorants, and also fillers such as talc and clay, may also be used. Preservatives, e.g, EDTA, generally at a level of less than 1% of the composition, may be incorporated in the cleansing products to prevent microbiological growth. Antibacterials can also be incorporated, usually at levels up to 1.5%.

Process for Making the Ultra Mild Toilet Bar

In order to make the product, an analysis of the surfactant paste is needed. To illustrate the process, an AGS paste with the following nominal analysis will be used.

Cationic Titration for $SO_3$ = 48.5% AGS
NaCl = 1.5%
Moisture = 43%

After the composition of the AGS paste is determined, the crutcher mix is calculated using the AGS/sarcosinate ratio of 4:1, 55% moisture in the crutcher mix and about 3.5% NaCl in the final bar.

Crutching

Assuming 200 lb (90.8 Kg) crutcher mix and the above AGS analysis.
1. Heat crutcher mix to 200° F. (93° C.) by adjusting steam and water valves.
2. Add 83.7 lbs. (38 Kg) of AGS paste.
3. Turn on agitator and recirculation pump.
4. When the AGS temperature is 130° F. (54° C.) add 12.0 lbs. (5.45 Kg) of stearic acid.
5. When the crutcher mix temperature is back up to 130° F. (54° C.) add 2.18 lbs. (991 g) of 50% NaOH.
6. Add 2-3 gal. (7.6–11.4 liters) of hot water (160°–180° F., 71°–82° C.) as needed to thin the crutcher mix to obtain good mixing.
7. Allow the crutcher contents to mix for about 20 minutes and maintain the temperature at 130°–140° F. (54°–60° C.).
8. Add 10.15 lbs. (4.61 Kg) of Hamposyl L-95 $C_{12}$ sarcosinate.
9. Add 2-3 gal. (7.6–11.4 liters) of hot water as needed for good mixing.
10. Maintain 140° F. (60° C.).
11. In a suitable container, slurry 2.71 lbs. (1.23 Kg) of JR-400 in hot water.
12. Add the JR-400 slurry to the crutcher; add more hot water as needed to get to 55% $H_2O$ in the crutcher.
13. Add 8.0 lbs. (3.63 Kg) of lauric acid.
14. Add 0.22 lbs. (101 g) of $TiO_2$.
15. Add 1.16 lbs. (527 g) of NaCl.
16. Mix for at least 20 min. and bring the crutcher mix temperature up to 175° F. (79° C).

Drying

The crutcher mix is dried on a atmospheric drum dryer. The optimum operating conditions are 3–4 rpm, 80 psi and approximately 310° F. (154° C.). The nip of the drums are set to give a fairly thin flake. The nip is increased to give thicker flake and to allow the higher moisture in the flake. Typical moisture for the flake is 2–3%. The three ways to regulate the moisture, in the order of preference, are (1) opening or closing the drum gap; (2) increasing or decreasing the drum speed; and (3) increasing or decreasing the steam pressure.

Amalgamating

The flakes are weighed and mixed in a batch amalgamator to obtain a uniform flake sample for moisture analysis. Once the percent water is known, water and perfume are added to bring the flakes up to final target formula. About ½% extra water is added to allow for losses during processing. The sticky, perfumed flakes are transferred to the mill hopper.

Milling

The 3-roll soap mills are set up with the first roll at 100° F. (38° C.) and the other 2 rolls at about 70° F. (21° C.). The soap is passed through the mills several times and forms sticky flakes. These flakes are put into a sealed plastic bag and placed in the 100° F. (38° C.) constant temperature room overnight. The flakes are milled one final time prior to plodding.

Plodding and Stamping

The plodder is set up with the barrel temperature at ambient to cold and the nose temperature at 120°–130° F. (49°–54° C.). The ideal plodder is a dual stage plodder that allows use of a vacuum of about 15-25 in. Hg. The plugs should be cut in 5" sections and stamped with a cold die block and stamp using a die liquor such as alcohol.

CLINICAL ASSESSMENT OF ULTRA MILD TOILET BAR

The clinical test procedure used to evaluate several toilet bar formulations for skin mildness is given below.

Clinical Mildness Arm Wash Test Procedure (2 Washes Per Day for Two Weeks for 23 Washes)

The washings were performed by technical personnel. Each panelist was assigned a set of two test products for washings. These bars were all kept under technical personnel control in plastic dishes. The test procedure is:
1. Wet the anterior portion (inside) of the forearm of the panelist with 90°–100° F. (32°–38° C.) water (6-8 grains hardness) from the elbow to the wrist.
2. Pick up and wet the bar.
3. Rub bar from wrist area up to the elbow and back down again in approximately 1 second. Repeat rubbing 5 more up-down cycles for a total of 6 cycles in 6 seconds.

4. Put bar aside and rub area in the same manner with the hand for 10 additional seconds (approximately 10 additional up-down cycles).
5. Rinse forearm thoroughly with tap water. Pat dry with clean paper towels.
6. Repeat procedure on other arm.

For Panelists on Water Treatment

1. Wet the anterior portion (inside) of the forearm with 90°–100° F. (32°–38° C.) water (6–8 grains hardness) from the elbow to the wrist.
2. Rub hand (up and down) on arm for 15 seconds.
3. Rinse forearm thoroughly with tap water. Pat dry with clean paper towels.

Test Product Formulations

The formulations of the products tested clinically are given in the Tables. The molar equivalents of only Example F are given in Table 3 to illustrate the stoichiometric ratios of several key ingredients. The moles of polymer are based on the average molecular weight of monomer containing one positive charge.

TABLE 2

| | Test Product Formulations | | | |
|---|---|---|---|---|
| Examples: | A 5% | C 0.5% JR-400 | F 3% JR-400 | G 1.5% JR-400 |
| Ingredients | JR-400 | | | |
| NaAGS | 36.0 | 36.0 | 48.14 | 48.74 |
| NaC$_{12}$ Sarconate | 9.5 | 9.5 | 11.07 | 11.21 |
| Stearic Acid | 24.5 | 24.5 | 9.58 | 10.22 |
| Lauric Acid | — | — | 6.39 | 6.81 |
| JR-400 | 5.0 | 0.5 | 3.08 | 1.56 |
| Dextrin | 8.7 | 14.2 | — | — |
| Unsulfonated Alcohol | 3.9 | 3.9 | 1.24 | 1.26 |
| Na Laurate | 0.4 | 0.4 | 0.49 | 0.50 |
| Na Soap (60/40 T/C) | — | — | 7.69 | 7.79 |
| NaCl | 3.4 | 3.4 | 3.29 | 4.03 |
| Na$_2$SO$_4$ | 1.6 | 1.6 | 1.24 | 1.26 |
| TiO$_2$ | 0.5 | 0.5 | 0.26 | 0.26 |
| Perfume | 0.5 | 0.5 | 1.03 | 1.04 |
| Water | 6.0 | 5.0 | 6.43 | 5.26 |

Figure 3:
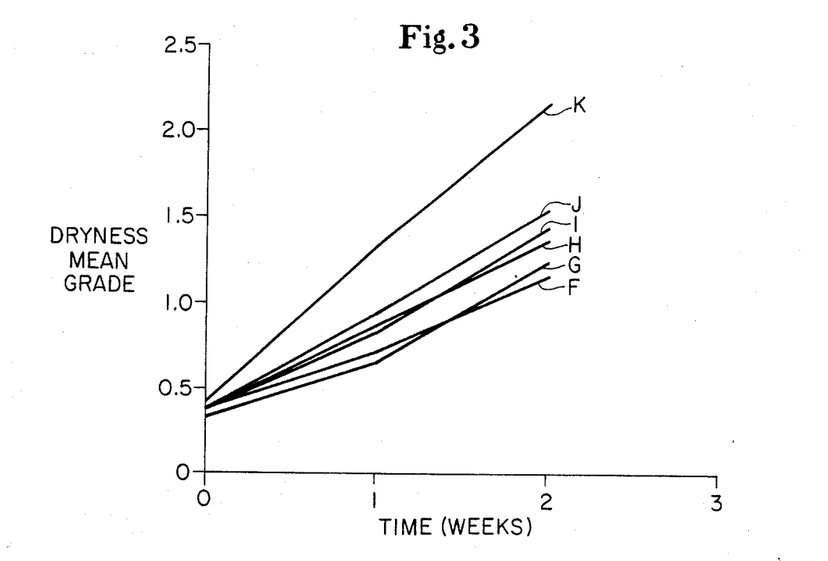

Example H (mildness results are shown in FIG. 3 as Curve H) is substantially the same formulation as Example G, except that the formulation contained no JR-400 polymer. Examples E and K are 50/50 tallow/coconut super fatted bar soap.

Example D is Dove ®, (a commercially available bar) which does not contain polymeric skin feel and polymeric skin mildness aids.

TABLE 3

| Molar Equivalents of Example F with 3% JR-400 | |
|---|---|
| Ingredient | m Moles/100 g Bar |
| Sodium Soap (60/40) | 27.7 |
| Sodium AGS | 116.0 |
| Unsulfonated Alcohol | 15.8 |
| Stearic Acid | 32.8 |
| Sodium Lauryl Sarcosinate | 36.7 |
| Sodum Laurate | 2.1 |
| Lauric Acid | 31.1 |
| Polymer JR-400 | 4.3 |

Note from Table 3 that the stoichiometric ratio of soap (27.7) to polymer (4.3) is about 7:1. It will be appreciated that the total synthetic surfactant to soap weight ratio in Example F reported in Table 2 is about 7.5:1, and the total moisturizer to soap ratio is about 2:1.

Clinical Test Skin Grading Scales

The forearm skin grading scales reported herein are set out below.

Forearm Grading Scale Skin Dryness

0 Perfect skin.
1.0 Patches of checking and/or slight powderiness and occasional patches of small scales may be seen. Distribution generalized.
2.0 Generalized slight powderiness. Early cracking or occasional small lifting scales may be present.
3.0 Generalized moderate powderiness and/or moderate cracking and lifting scales.
4.0 Generalized heavy powderiness and/or heavy cracking and lifting scales.
5.0 Generalized high cracking and lifting scales. Eczematous change may be present. Powderiness may be present but not prominent. May see bleeding crack.
6.0 Generalized severe cracking. Eczematous change may be present. Bleeding cracks may be present. Scales large, may be beginning to disappear.

| Forearm Grading Scales | |
|---|---|
| Skin Erythema | Skin Smoothness |
| 0 No redness | 0 Very high smoothness/slick |
| 1.0 Barely detectible redness | 1.0 extreme smoothness |
| 2.0 Slight redness | 2.0 substantial smoothness |
| 3.0 Moderate redness | 3.0 Moderate smoothness |
| 4.0 Heavy or substantial redness | 4.0 Slight smoothness |
| 5.0 Severe redness | 5.0 Barely detectible smoothness |
| 6.0 Extreme redness | 6.0 No smoothness |

The term "generalized" as used herein means that more than 50% of the surface area of the forearm exhibits the attribute. Whole unit skin grades reflect generalized condition. Half units are used to represent intermediate conditions.

Clinical Test Results

Figure 2:
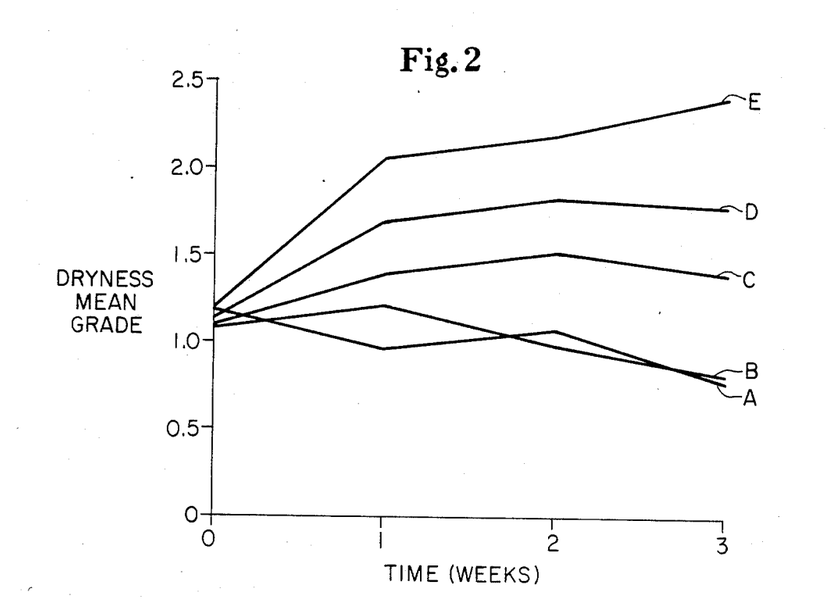
FIGS. 2–5 show comparative clinical mildness results of various cleansing compositions.

The clinical mildness test results expressed in terms of skin grades for dryness, erythema, and smoothness are shown below in Table 4 and the skin dryness grades are plotted vs. time in FIG. 3. Skin dryness grades from a second clinical test are shown in a similar fashion in FIG. 2. Water treatment results are shown as curves B and I in FIGS. 2 and 3, respectively. Curves D and J are the results of DOVE ® (a commercially available bar).

TABLE 4

| | Two Week Clinical Results Skin Grades | | |
|---|---|---|---|
| Example | Dryness | Erythema | Smoothness |
| F | 1.16 H-K | 1.04 J,K | 2.76 H |
| G | 1.25 J,K | 1.07 J,K | 2.75 |
| H | 1.37 F,J,K | 1.19 K | 2.58 F,I,K |
| I | 1.44 F,K | 1.23 K | 2.81 H |
| J | 1.55 F,G,K | 1.28 F,G,K | 2.72 K |
| K | 2.17 F,K | 1.75 F-J | 2.87 I,J |

In Table 4 the visual skin grades for dryness, erythema and tactile grades for smoothness are all assigned from a six point scale (0–6), the lower the grade the better the skin mildness. Letter codes indicate statistically significant ($\alpha = 0.05$) differences. Also see FIGS. 2 and 3 for a graphic report of these data.

These data show that the toilet skin cleansing bars of this invention (Examples A, G and F) result in the desired mild skin cleansing action with improved skin feel and moisturization benefits. Note that Example A listed in Table 2 is as mild as "B" water (see FIG. 2). It will be appreciated that bars F and G are actually milder than water (I) as shown in Table 4 and FIG. 3. It will also be appreciated that the toilet skin cleansing bars A, G and F of the present invention are not only mild but also have excellent bar smear and lather performance.

Figure 4:
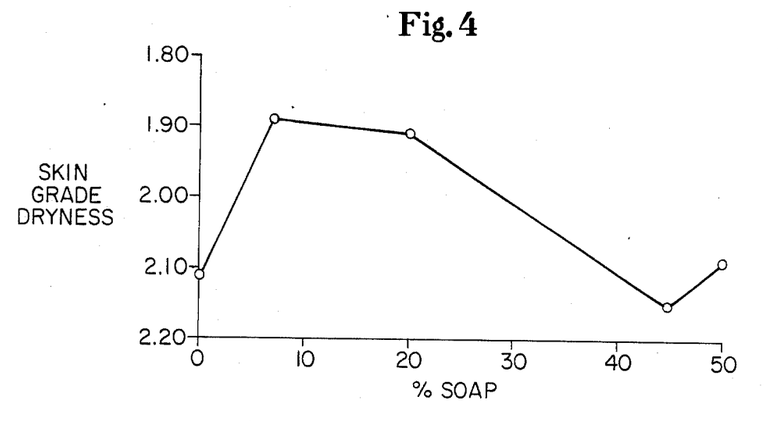
Figure 5:
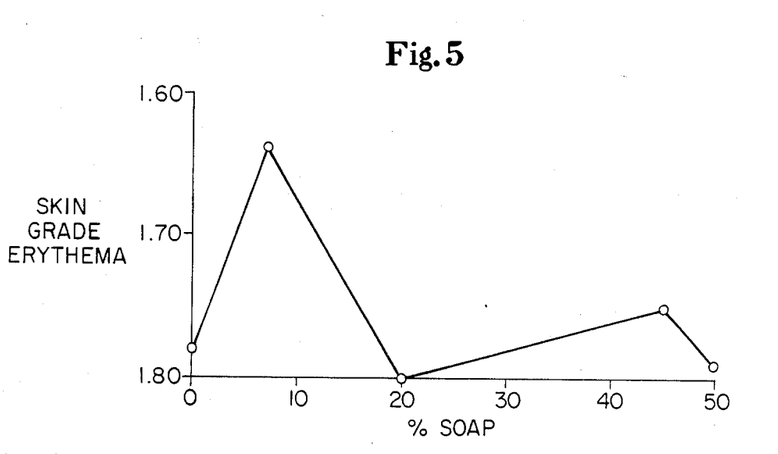

It will be appreciated that the addition of selected levels of soap surprisingly provide improved skin mildness. Examples L-P set out in Table 5 show the selected levels. The effect of varying amounts of soap in this invention on clinical skin condition is demonstrated in Table 6. The skin dryness and skin erythema grades are respectively plotted in FIGS. 4 and 5 vs. soap level. The overall conclusion from these data is that selected levels of soap surprisingly provide additional clinical mildness benefit for reduced skin dryness and erythema and enhanced skin smoothness. The reduced skin dryness benefit shown in FIG. 4 is maximum at the 7-20% soap level, whereas the reduced erythema shown in FIG. 5 (and smoothness benefit in Table 6) is maximum at about the 7% soap level.

TABLE 5

| Test Product Ingredients | Test Product Formulations | | | | |
|---|---|---|---|---|---|
| | L | M | N | O | P |
| Na AGS | 43.15 | 43.15 | 33.15 | 16.00 | 9.15 |
| NaC$_{12}$ Sarcosinate | 10.80 | 10.80 | 8.30 | — | 2.30 |
| Stearic Acid | 16.00 | 11.50 | 11.84 | 12.89 | 12.73 |
| Lauric Acid | 10.67 | 7.67 | 7.89 | 8.59 | 8.49 |
| JR-400 | 3.00 | 3.00 | 3.00 | 3.00 | 3.00 |
| Unsulfonated Alcohol | 0.83 | 0.83 | 0.64 | 0.31 | 0.18 |
| Na Laurate | 0.48 | 0.48 | 0.37 | — | 0.10 |
| Na Soap | — | 7.50 | 20.05 | 45.01 | 49.99 |
| NaCl | 4.04 | 4.04 | 4.04 | 4.00 | 4.03 |
| Na$_2$SO$_4$ | 1.20 | 1.20 | 0.92 | 0.44 | 0.25 |
| TiO$_2$ | 0.25 | 0.25 | 0.25 | 0.25 | 0.25 |
| Perfume | 1.00 | 1.00 | 1.00 | 1.00 | 1.00 |
| Water | 8.50 | 8.50 | 8.50 | 8.50 | 8.50 |
| Miscellaneous | 0.08 | 0.08 | 0.06 | — | 0.02 |

TABLE 6

| Test Product | Two Week Clinical Results Skin Grades | | | |
|---|---|---|---|---|
| | % Soap | Dryness | Erythema | Smoothness |
| L | — | 2.11 | 1.78 | 1.79 |
| M | 7.50 | 1.89 | 1.64 | 1.66 |
| N | 20.05 | 1.91 | 1.80 | 1.76 |
| O | 45.01 | 2.15 | 1.75 | 1.73 |
| P | 49.99 | 2.09 | 1.79 | 1.73 |

Laboratory Assessment of Bar Performance

The following test procedures are used to evaluate the critical bar performance attributes of lather volume and bar firmness during use.

Bar Soap Firmness Test

The bar soap firmness test measures two quantitative parameters of bar firmness after sitting in a wet soap dish for 16 hours: (1) depth of bar surface softening and (2) amount of bar messiness by weight percent of initial bar weight.

Equipment

The following equipment is used:
1. "Alathon" rectangular plastic soap dishes (U.S. Pat. No. 2,842,178) with low ridges.
2. Precision Scientific Co. penetrometer with ball shaft, 300 gram weight.
3. Analytical weight balance.
4. Scraper or spatula for removing gelatinous layer.
5. Paper towels.

Procedure

The following procedure is used:
1. Test bar(s) are weighed to establish an initial dry weight data point.
2. If desired, initial dry bar hardness/softness may be determined by penetrometer with cone shaft and 200 gram weight for penetration measurement.
3. Bar(s) are placed centrally on soap dishes containing 5 ml. of distilled water at room temperature. Rock the dish to break water tension.
4. Store overnight (approximately 18 hours) in standard room conditions of temperature and humidity (80° F./80% RH).
5. Next morning, remove bar(s) with a careful vertical lift and invert for testing.
6. Run ball penetrometer reading on the gelatinous surface, generally three readings in a triangular design; record the average mm depth reading of gelatinous layer. The shaft ball is cleaned with a tissue after each reading.
7. Bar(s) are then carefully scraped to remove the gelatinous layer down to the solid surface. Do not use enough force to remove any of the solid surface area. Slight remaining gelatinous soap may be wiped from bar with paper towels until surface appears firm and somewhat dry.
8. Bar(s) are then allowed to openly dry out on bench surface for no more than one hour.
9. Bar(s) are then weighed to determine the difference from the initial dry untested weight. The weight difference divided by the original weight is calculated into % weight loss or % gelatinous smear weight. Data is recorded.
10. Comparison of any given series of data points obtained will illustrate a formula characteristic that may tend to relate to poorer smear or "messiness" attribute. Averaging of historical data on control type formulas (such as an existing National brand formula) can be used to establish a benchmark for comparison.

Bar Soap Handwash Lather Volume Test

The handwash lather test is used to provide in-use lather volume measurements for the lather performance of skin cleansing bars. The test measures both the ultimate lather volume generated and the volume which is generated after a very short lathering period (to reflect lathering ease). The lather volumes are generated under both soil-loaded and nonloaded conditions.

Synthetic soil is used for the soil-loaded lather volume test reported herein. Its formula and procedure for making it are set out below.

TABLE 9

| Synthetic Soil | |
|---|---|
| Ingredients | Wt. % |
| Hyfac 430[a] | 1.87 |
| Lauric Acid[b] | 1.42 |

TABLE 9-continued

Synthetic Soil

| Ingredients | Wt. % |
|---|---|
| Neo-fat 14[c] | 5.68 |
| Neo-fat 16[d] | 11.16 |
| Neo-fat 18[e] | 5.40 |
| Neo-fat 90-04[f] | 9.81 |
| Industrene 226[g] | 1.26 |
| Paraffin Wax | 7.30 |
| Squalane[h] | 3.70 |
| Lanolin Anhydrous | 19.40 |
| Coconut Oil | 3.30 |
| Tallow | 29.70 |
|  | 100.00% |

[a]Emery Industries, Inc., Cincinnati, Ohio
[b]Emery Industries, Inc., Cincinnati, Ohio
[c]Armour Industrial Chemical Co., Chicago, Illinois
[d]Armour Industrial Chemical Co., Chicago, Illinois
[e]Armour Industrial Chemical Co., Chicago, Illinois
[f]Armour Industrial Chemical Co., Chicago, Illinois
[g]Humko Products, Memphis, Tennessee
[h]Robeco Chemicals, Inc., New York, New York

Procedure

1. Heat above materials together stirring continuously between 160°–175° F.
2. Mix 25 parts of above formula with 25 parts of a 5% to 80% tallow/20% coconut soap solution and 50 parts of distilled water at 150° F.
3. Cool mixture to room temperature while stirring constantly.
4. Store in covered glass container.

Equipment

The following equipment is used:
1. Water source and sink with temperature control. The water source should be medium hardness (6–9 grain/gallon) for most testing, although water of lower and higher hardness can be used for special purposes.
2. Synthetic soil (see Table 9).
3. Paper towels.
4. Test bars.
5. Control bars (i.e., usually marketed brands such as CAMAY ® or the bar of Example D).

Procedure

The following procedure is used:
1. Set temperature at 95°–100° F.
2. Rub 0.22 cc of soil on hands (if doing soil-loaded test).
3. Wet hands.
4. Rotate bar 3 times in both hands.
5. Add a little water, rub both hands 5 times.
6. Rotate hands 3 times (without soap), grade for flash volume.
7. Rotate 7 more times, grade for ultimate volume.
8. Collect lather and deposit on sink top.
9. Compare volume with standard bar target volume and assign grade.

Grading Scale

| | Non-Soil Loaded | Soil-Loaded |
|---|---|---|
| 10 | Very much higher than target | |
| 9 | Higher than target | |
| 8 | Target volume* | Very much higher than target |
| 7 | Lower than target | Higher than target |
| 6 | Very much lower than target | Target volume* |
| 5 | Unacceptably lower than target | Slightly lower than target |
| 4 | Unacceptably lower than target | Lower than target |
| 3 | Unacceptably lower than target | Very much lower |
| 2 | Unacceptably lower than target | Unacceptably low |

*Based on 50 tallow/50 coconut - 7% free fatty acid bar.

TABLE 7

Bar Formulations

| Example | Na AGS Wt. % | NaC$_{12}$ Sarcosinate Wt. % | Free Fatty Acid Stearic Wt. % | Free Fatty Acid Lauric Wt. % | Soap Wt. % | JR-400 Wt. % |
|---|---|---|---|---|---|---|
| 1 | 42 | 9.0 | 18 | — | — | 0.5 |
| 2 | 43 | 10.8 | 15 | 10 | — | 3.0 |
| 3 | 43 | 11.4 | 10 | 6.8 | 7.0 | 3.0 |
| 4 | Camay ® | | | | | |
| 5 | Dove ® | | | | | |

TABLE 8

Bar Firmness and Hand Lather

| Example | Penetrometer mm | Smear Wt. % of Bar Wt. | Hand Lather Ultimate Volume w/o Soil | Hand Lather Ultimate Volume Soil | Hand Lather Flash Volume w/o Soil | Hand Lather Flash Volume Soil |
|---|---|---|---|---|---|---|
| 1 | 2.9 | 8.7 | 8 | 3 | 8 | 2.5 |
| 2 | 2.6 | 6.5 | 8 | 2.5 | 8 | 2.5 |
| 3 | 2.3 | 7.2 | 8 | 5 | 8 | 4 |
| 4 | 1.1 | 3.2 | 8 | 6.5 | 8 | 6.5 |
| 5 | 1.8 | 5.0 | 8 | 3 | 8 | 3 |

The results listed in Tables 7 and 8 show the importance of utilizing the preferred ratio of stearic to lauric fatty acids to achieve an acceptable level of firmness and the importance of utilizing soap to achieve an acceptable soil-loaded lather performance. The acceptable levels of bar firmness are expressed as a penetrometer value of equal to or less than 2.7 and smear weight of equal to or less than 7.5. The acceptable levels of hand lather are: ultimate volume, without soil equal to or greater than 7.5; with soil, equal to or greater than 4. Flash volume acceptable levels are: without soil, equal to or greater than 7.5; with soil, equal to or greater than 4.

Example 1 described a sodium AGS bar formula with acceptable mildness but with poor lather and firmness performance. Example 2 demonstrates the advantage of using a 3:2 ratio of stearic:lauric fatty acids. Example 3 demonstrates the benefit of neutralizing the fatty acids in situ forming 7% soap to boost the soil-loaded lather. Example 4 is a 50/50 tallow/coconut superfatted soap bar which demonstrates very acceptable bar firmness and lather properties. Example 5 is the same as Example D which shows acceptable firmness and lather properties.

Bar Soap Blender Lather Volume Method

Purpose

This quantitative blender lather volume method is used to compliment hand lathering evaluations of different soap formulations.

Equipment

1. Specially designed 500 ml graduate cylinder adapted with blender impeller.
2. Waring Blender Base No. 7011-31BL92 with high/low speed switch.
3. Variac Voltage Regulator

Procedure

1. Dissolve 5% by weight of the bar material to be evaluated in distilled water by heating to 150° F. (65.7° C.).
2. Add 10 mls of soap solution to 90 mls of water both at 38° C. in a 100 ml graduate.
3. Immediately pour resultant 0.5% solution into blender graduate.
4. Set blender to run at about 4700 rpm's (high speed) and blend solution for fifteen seconds.
5. After blending read lather height on cylinder.
6. Replicate a minimum of three times and average.

Figure 6:
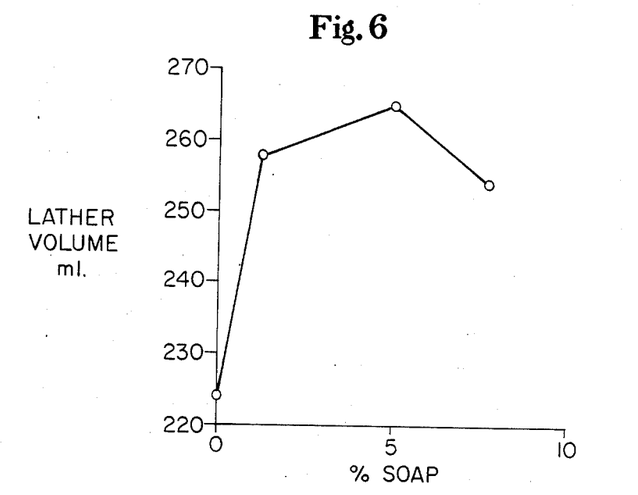
FIG. 6 shows lather volume as a function of selected soap levels.

The effect of varying the amount of soap in Example L (by converting free fatty acid to soap with NaOH) on lather volume (using the blender method) is shown in FIG. 6. This curve demonstrates that lather volume is increased by the selected levels of soap in the formulation.

Thus, it has been demonstrated that an ultra mild skin cleansing composition can be made with selected mild synthetic surfactants; selected moisturizers; polymeric skin feel and mildness aids; and selected levels of soap.

What is claimed is:

1. An ultra mild skin cleansing toilet bar composition comprising:
    A. 20-70% mild synthetic surfactant;
    B. 10-30% moisturizer;
    C. 0.1-5% polymeric skin mildness aid, and
    D. 5.5-25% soap;
    wherein said synthetic surfactant and said soap have a weight ratio of from 2:1 to 12:1; and
    wherein said moisturizer to soap have a weight ratio of from 1:1 to 7:1;
    wherein said moisturizer consists essentially of stearic and lauric acid having a weight ratio of 2:1 to 1:1.5; and
    wherein said soap to polymer have a stoichiometric ratio of from about 1:1 to about 17:1 on a charge basis.

2. The ultra mild skin cleansing composition of claim 1 wherein said synthetic to soap ratio is 4:1 to 10:1.

3. The ultra mild skin cleansing composition of claim 1 wherein said synthetic to soap ratio is 6:1 to 9:1.

4. The ultra mild skin cleansing composition of claim 1 wherein said moisturizer to soap ratio is from 1:1 to 4:1.

5. The ultra mild skin cleansing composition of claim 1 wherein said soap to polymer stoichiometric ratio is from 4:1 to 10:1.

6. The ultra mild skin cleansing composition of claim 1 wherein said mild surfactant is selected from the group consisting of:
    alkyl glyceryl ether sulfonate (AGS);
    anionic acyl sarcosinates;
    methyl acyl taurates;
    N-acyl glutamates;
    alkyl glucosides;
    acyl isethionates;
    alkyl sulfosuccinate;
    alkyl phosphate ester;
    alkyl ether sulfate;
    ethoxylated alkyl phosphate esters;
    methyl glucose esters;
    protein condensates;
    mixtures of ethoxylated alkyl sulfates and alkyl amine oxides;
    betaines;
    sultaines; and
    mixtures thereof;
    said mild synthetic surfactant containing at least one surfactant selected from mild anionic or mild amphoteric surfactants.

7. The ultra mild skin cleansing composition of claim 1 wherein said mild surfactant is an alkyl gylceryl ether sulfonate/sarcosinate mix having ratio of 1:1 to 5:1.

8. The ultra mild skin cleansing composition of claim 7 wherein said alkyl glyceryl ether sulfonate/sarcosinate has a ratio of 2:1 to 4:1.

9. The ultra mild skin cleansing composition of claim 1 wherein said concentrate also contains a co-surfactant selected from the group consisting of nonionic, amphoteric betaine or amphoteric sultaine, and wherein the mild surfactant and the co-surfactant have a ratio of 1:1 to 5:1, and wherein said mild synthetic surfactant is other than betaine or sultaine.

10. The ultra mild skin cleansing composition of claim 1 wherein said composition contains from 5.5-20% soap and wherein said soap is made in situ from free fatty acids and a base selected from KOH, $Mg(OH)_2$, NaOH and triethanolamine.

11. The ultra mild skin cleansing composition of claim 10 wherein said composition contains from 10-30% fatty acids and wherein said base is selected from NaOH and triethanolamine.

12. The ultra mild skin cleansing composition of claim 11 wherein said moisturizer is a mixture of stearic and lauric acids having a ratio of from 2:1 to 1:1 and is present in said composition at a level of from 15-20%.

13. The ultra mild skin cleansing composition of claim 1 wherein said moisturizer to soap ratio is from 2:1 to 4:1.

14. The ultra mild skin cleansing composition of claim 1 wherein said polymer is a cationic polymer.

15. The composition of claim 1 wherein said polymer is selected from cationic and nonionic cellulosic resins.

16. The ultra mild skin cleansing composition of claim 1 wherein said polymer is selected from the group consisting of cationic and nonionic polysaccharides; cationic and nonionic homopolymers and copolymers derived from acrylic and/or methacrylic acid; cationic copolymers of dimethyldiallylammonium chloride and acrylic acid; cationic homopolymers of dimethyldiallylammonium chloride; cationic polyalkylene and ethoxypolyalkylene imines, and mixtures thereof.

17. The ultra mild skin cleansing composition of claim 1 wherein said polymer is a cationic guar gum.

18. The ultra mild skin cleansing composition of claim 1 wherein said polymer is present at 0.3-4% by weight; and said moisturizer is free fatty acids is present at 10-30% by weight of said composition.

19. The ultra mild skin cleansing composition of claim 1 wherein said mild synthetic surfactant is present at a level of 40-70% of said composition, and wherein said mild synthetic surfactant has a Relative Skin Barrier Penetration Value of from about 7 to about 75.

20. The ultra mild skin cleansing composition of claim 1 wherein said mild synthetic surfactant is present at a level of 50-65% of said composition and wherein said synthetic surfactant has a Relative Skin Barrier Penetration Value of less than 50.

21. The ultra mild skin cleansing composition of claim 1 wherein
said mild surfactant is present at 40-70%;
said polymer at 1.5-4%; and
said soap at 6-15%.

22. The ultra mild skin cleansing composition of claim 20 wherein said composition contains from 6-8% soap, 12-25% moisturizer, and 2-5% polymeric skin feel aid.

23. An ultra mild skin cleansing toilet bar composition comprising:
A. 20-70% mild snythetic surfactant;
B. 10-30% moisturizer; and
C. 0.1-5% polymeric skin feel aid;
wherein said moisturizer consists essentially of stearic and lauric acids having a ratio of 2:1 to 1:1.5.

24. The ultra mild skin cleansing composition of claim 22 wherein Component A is selected from the group consisting of mild surfactants:
alkyl glyceryl ether sulfonate (AGS);
anionic acyl sarcosinates;
methyl acyl taurates;
N-acyl glutamates;
alkyl glucosides;
acyl isethionates;
alkyl sulfosuccinate;
alkyl phosphate esters;
alkyl ether sulfates;
ethoxylated alkyl phosphate esters;
methyl glucose esters;
protein condensates;
mixtures of ethoxylated alkyl sulfates and alkyl amine oxides;
betaines;
sultaines; and
mixtures thereof;
said mild synthetic surfactant containing at least one surfactant selected from mild anionic or mild amphoteric surfactants.

25. The ultra mild skin cleansing composition of claim 22 wherein said mild surfactant is an alkyl glyceryl ether sulfonate/sarcosinate mix having ratio of 1:1 to 5:1.

26. The ultra mild skin cleansing composition of claim 3 wherein said alkyl glyceryl ether sulfonate/sarcosinate has a ratio of 2:1 to 4:1.

27. The ultra mild skin cleansing composition of claims 1, 3, 4, 5, 8, 10, 11, 18, 20, 21, 22 or 23 wherein said bar has a firmness penetrometer value of 2.7 or less and a smear weight value of 7.5 or less.

* * * * *